United States Patent [19]

Hashimoto et al.

[11] 4,323,505
[45] Apr. 6, 1982

[54] POLYALKYLHYDROXYCHROMENE AND PROCESS FOR PREPARING THE SAME

[75] Inventors: Isao Hashimoto; Hirohiko Nambu, both of Iwakuni, Japan

[73] Assignee: Mitsui Petrochemical Industries, Ltd., Tokyo, Japan

[21] Appl. No.: 163,660

[22] Filed: Jun. 27, 1980

[30] Foreign Application Priority Data

Jun. 27, 1979 [JP] Japan .................. 54-80133

[51] Int. Cl.³ .................. C07D 311/70; C07D 311/04
[52] U.S. Cl. ...................... 260/345.2; 71/88
[58] Field of Search ...................... 260/345.2

[56] References Cited

FOREIGN PATENT DOCUMENTS 822659 10/1959 United Kingdom ............. 260/345.2

OTHER PUBLICATIONS

Bergel et al., Chem. Abstract, 33, 586² (1939).

Primary Examiner—Nicky Chan
Attorney, Agent, or Firm—Sughrue, Mion, Zinn, Macpeak and Seas

[57] ABSTRACT

A compound of the formula (I)

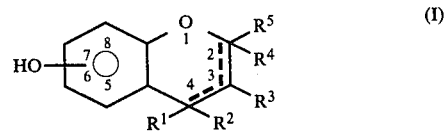

wherein $R^1$ and $R^5$ each represents an alkyl group having 1 to 3 carbon atoms; $R^2$, $R^3$ and $R^4$ each represents a hydrogen atom or an alkyl group having 1 to 3 carbon atoms and wherein the bonding at the 2-3 position is a single bond and that at the 3-4 position is a double when the substitution of hydroxy group is at the 5-position or the bonding at the 2-3 position is a double bond and that at the 3-4 position is a single bond when the substitution of hydroxy group is at the 7-position; with the proviso that $R^2$ and $R^4$ should not be a hydrogen atom or an alkyl group simultaneously and process for preparing same are disclosed. The compound is useful as a herbicide and fungicide and as an intermediate for preparing agricultural chemicals, etc.

4 Claims, No Drawings

POLYALKYLHYDROXYCHROMENE AND PROCESS FOR PREPARING THE SAME

BACKGROUND OF THE INVENTION

1. Field of the Invention

The present invention relates to polyalkylhydroxychromenes, i.e., 2,2,4-trialkyl-5-hydroxy-2H-chromenes, 2,4,4-trialkyl-7-hydroxy-4H-chromenes, 2,3,4,4-tetraalkyl-7-hydroxy-4H-chromenes and 2,2,3,4-tetraalkyl-5-hydroxy-2H-chromenes, and process for preparing the same. More particularly, the present invention relates to polyalkylhydroxychromenes which can be used as a herbicide and a fungicide and as an intermediate for preparing agricultural chemicals, medicines, perfumes and additives to resins and as a monomer for preparing polymers, and to process for preparing the same.

2. Description of the Prior Art 2,2,4,8-Tetramethyl-2H-chromene and 2,2,4-trimethyl-7-hydroxy-2H-chromene and their preparation form mesityl oxide and o-cresol or resorcin are known form *Chemical Abstracts* 76, 59369z (1972). As far as is known no utility of the above compounds has been reported yet.

Compounds which, on one hand, have a utility in themselves and, on the other hand, are useful as intermediates for preparing various useful compounds are very desirable in view of economy of chemical industry.

SUMMARY OF THE INVENTION

An object of the present invention is to provide novel polyalkylhydroxychromenes.

Another object of the present invention is to provide a process for preparing polyalkylhydroxychromenes.

As a result of extensive research it has been found that some polyalkylhydroxychromenes have various utility and that these compounds can be prepared in good yield by condensing resorcin with an aliphatic ketone or tertiary alcohol in the presence of an acid catalyst or a basic catalyst, or thermally decomposing polyalkyl-(2,4-dihydroxyphenyl)hydroxychroman which is obtained by the condensation of resorcin with an aliphatic ketone.

Thus, the present invention provides a novel compound of the formula (I)

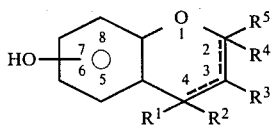

wherein $R^1$ and $R^5$ each represents an alkyl group having 1 to 3 carbon atoms; $R^2$, $R^3$ and $R^4$ each represents a hydrogen atom or an alkyl group having 1 to 3 carbon atoms and wherein the bonding at the 2-3 position is a single bond and that at the 3-4 position is a double bond when the substitution of hydroxy group is at the 5-position, or the bonding at the 2-3 position is a double bond and that at the 3-4 position is a single bond when the substitution of hydroxy groups is at the 7-position; with the proviso that $R^2$ and $R^4$ should not be a hydrogen atom or an alkyl group simultaneously.

Also, the present invention provides a process for preparing a compound of the formula (I)

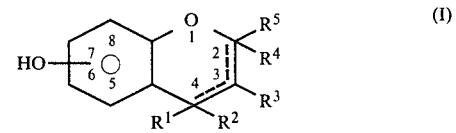

wherein $R^1$, $R^2$, $R^3$, $R^4$ and $R^5$, the bondings at the 2-3 and 3-4 positions and the substitution of hydroxy group are as defined above, which comprises reacting resorcin with an aliphatic ketone or tertiary alcohol, or thermally decomposing polyalkyl-(2,4-dihydroxyphenyl)-hydroxychroman.

DETAILED DESCRIPTION OF THE INVENTION

The term "alkyl" as used herein refers to an alkyl group having 1 to 3 carbon atoms such as methyl, ethyl, propyl and isopropyl.

The compounds represented by the formula (I) above are novel compounds and are useful not only as an intermediate compound for preparing agricultural chemicals such as herbicides, fungicides, etc., medicines, perfumes, additives to thermoplastic resins, e.g., polyolefins, but also as a herbicide or fungicide in itself.

For example, the compounds of the present invention represented by the formula (I) above can be used for preparing O-alkyl S-alkyl O-(polyhydroxybenzopyranyl)phosphorothioates such as O-ethyl S-ethyl O-(2,4,4-trimethyl-1,4-benzopyran-7-yl)phosphorothioate which is a novel insecticide effective agianst diamond-back moth (*Plutella maculipennis*).

Further, the compounds of the present invention represented by the formula (I) above exhibit an excellent controlling effect on fungi which cause downy mildew of cucumber and on paddy field and upland field weeds such as *Cuperus difformis*, lambsquarters, etc. superior to known compounds having a similar chemical sutructure.

Because of the presence of carbon-carbon double bond in the molecule, the compounds of the present invention are susceptible to cation polymerization and can be used for producing homopolymers or copolymers together with aliphatic or aromatic olefin comonomer copolymerizable therewith. Since the homopolymers and copolymers have a phenolic hydroxy group, they can be used as a weatherability improving agent, a water resistance improving agent, a coating strength improving agent, etc. for various polymer coatings. Further, the homopolymers and copolymers derived from the compounds of the present invention have a melt viscosity lower than that of similar polymers having same level of softening point and thereofore, they are advantageous in that processability is much improved.

Representative examples of the compounds represented by the formula (I) according to the prsent invention include the following compounds:

2,4,4-Trimethyl-7-hydroxy-4H-chromene
2,4,4-Triethyl-3-methyl-7-hydroxy-4H-chromene
2,4,4-Tri-n-propyl-3-ethyl-7-hydroxy-4H-chromene
2,2,4-Trimethyl-5-hydroxy-2H-chromene
2,2,4-Triethyl-5-hydroxy-2H-chromene
2,2,4-Tri-n-propyl-5-hydroxy-2H-chromene
2,2,4-Tri-isopropyl-5-hydroxy-2H-chromene
2,4-Diethyl-2-methyl-5-hydroxy-2H-chromene
2,4-Di-n-propyl-2-methyl-5-hydroxy-2H-chromene 2,4-Di-isopropyl-2-methyl-5-hydroxy-2H-chromene
2,2,3,4-Tetramethyl-5-hydroxy-2H-chromene
2,2,3,4-Tetraethyl-5-hydroxy-2H-chromene
2,2,3,4-Tetra-n-propyl-5-hydroxy-2H-chromene
2,2,3,4-Tetra-isopropyl-5-hydroxy-2H-chromene
2,2,4-Triethyl-3-methyl-5-hydroxy-2H-chromene
2,4-Di-isopropyl-2-ethyl-3-methyl-5-hydroxy-2H-chromene Of the above compounds, 2,4,4-trimethyl-7-hydroxy-4H-chromene, and 2,2,4-trimethyl-5-hydroxy-2H-chromene are particularly preferred.

The compounds of the formula (I) according to the present invention are novel compounds and their chemical structure can be determined by elemental analysis, mass spectral analysis, infrared absorption spectral analysis and $^1$H nuclear magnetic resonance spectral analysis.

Generally, proportion of the component elements (empirical formula) is obtained by elemental analysis and molecular weight is obtained by determining the mass number m/e (M$^+$) of major peak in the mass spectrum.

In the infrared absorption spectral analysis (IR) a broad, strong expansion and contraction oscillation which is ascribable to a phenolic hydroxy group is observed at about 3,600 to 3,000 cm$^{-1}$. Further, an expansion and contraction oscillation which is ascribable to C=C is observed at about 1,630 to 1,660 cm$^{-1}$ for 2H-chromene derivatives and that which is ascribable to C=C in the unsaturated ether bond (C=C—O—) is detected at about 1,700 to 1,715 cm$^{-1}$ for 4H-chromene derivatives of the formula (I) above.

The chemical structure of the compounds of the present invention can be determined by $^1$H nuclear magnetic resonance spectra measured in CDCl$_3$ as a solvent.

For example, in the case of the compound of the formula (I) wherein R$^1$, R$^2$ and R$^5$ each represents a methyl group and R$^3$ and R$^4$ each represents a hydrogen atom, signals are observed which are ascribable to various protons in the formula (II$_a$) below.

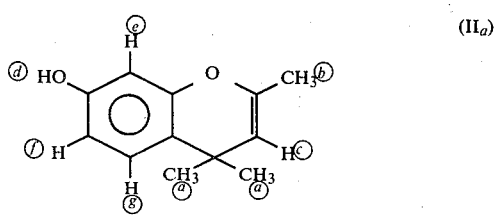

i.e., a signal ascribable to proton (d) at 5.15 δ (singlet); signals ascribable to protons (e), (f) and (g) at 6.35 δ (doublet, J$_{e,f}$=2 Hz), 6.50 δ (double of doublet, J$_{f,e}$=2 Hz, J$_{f,g}$=8 Hz) and 7.10 δ (doublet, J$_{g,f}$=8 Hz), respectively; signal ascribable to 6 equivalent protons (a) of two methyl groups attached to the 4-position at 1.25 δ (singlet); a signal ascribable to 3 protons (b) of methyl group at the 2-position at 1,83 δ (singlet); and proton (c) at the 3-position at 4.50 δ (singlet). From the above $^1$H nuclear magnetic resonance spectra the compound is confirmed to have the chemical structure represented by the formula (II$_a$) above. The chemical structure of other 4H-chromene compounds represented by the formula (I) wherein R$^1$, R$^2$, R$^3$, R$^4$ and R$^5$ have meanings different from those of the compound of the formula (II$_a$) can be determined similarly.

Also, in the case of the compounds of the formula (I) wherein R$^1$, R$^4$ and R$^5$ each represents a methyl group and R$^2$ and R$^3$ each represents a hydrogen atom, signals are observed which are ascribable to various protons in the formula (II$_b$) below

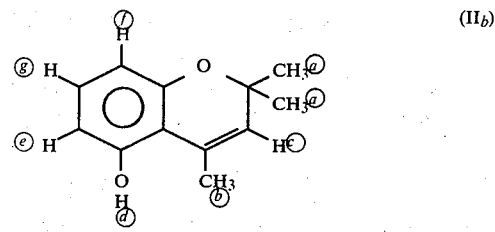

i.e., a signal ascribable to proton (a) of methyl group at the 2-position at 1.37 δ (singlet, 6H); a signal ascribable to proton (b) of methyl group at the 4-position at 2.20 δ (singlet, 3H); a signal ascribable to proton (c) at the 3-position at 5.33 δ (singlet, 1H); a signal ascribable to proton (d) of phenolic hydroxy group at 5.73 δ (singlet, 1H); signals ascribable to protons (e), (f) and (g) attached to the benzene ring at 6.25 δ (doublet, 1H, J=9 Hz), 6.48 δ (doublet, 1H, J=9 Hz) and 6.91 δ (triplet, 1H, J=9 Hz). The chemical structure of other 2H-chromene compounds represented by the formula (I) wherein R$^1$, R$^2$, R$^3$, R$^4$ and R$^5$ have meanings different from those of the compounds of the formula (II$_b$) can be determined similarly.

The compounds of the present invention represented by the formula (I) can be prepared by various alternative procedures from resorcin and an aliphatic ketone or tertiary alcohol or by thermal decomposition of polyalkyl-(2,4-dihydroxyphenyl)hydroxychroman.

Of the compounds of the formula (I), compounds represented by the formula (III) below.

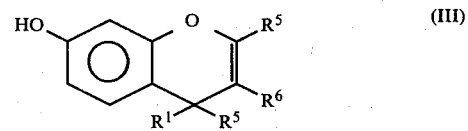

wherein R$^1$ and R$^5$ have the same meaning as defined above, and R$^6$ represents a hydrogen atom or an alkyl group having a carbon atom number smaller than that of R$^1$ by one, can be prepared according to Reaction Scheme-1 below.

Reaction Scheme-1

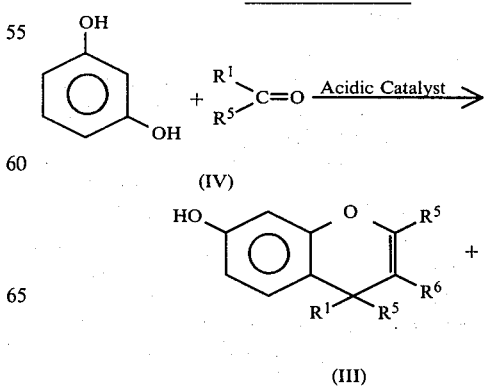

-continued
Reaction Scheme-1

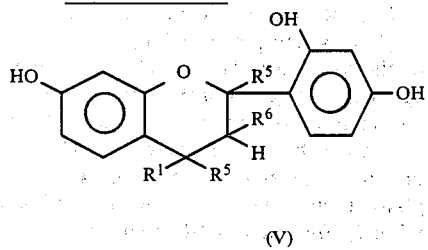

(V)

In the Reaction Scheme-1 above, $R^1$, $R^5$ and $R^6$ have the same meaning as defined above.

With respect to starting materials, no restriction is posed to the kind of resorcin and any resorcin can be used as a starting material irrespective of the manner in which it is produced.

Examples of suitable aliphatic ketone of the formula (IV) which can be used as starting material for preparing the compound of the formula (III) include acetone, methyl ethyl ketone, diethyl ketone, ethyl propyl ketone, dipropyl ketone, etc. Of these ketones, acetone is preferred.

Examples of suitable acidic catalyst used in the condensation reaction according to Reaction in Scheme-1 above include Brønsted acids such as sulfuric acid, hydrochloric acid, phosphoric acid, benzenesulfonic acid, toluenesulfonic acid, etc., solid acid catalysts such as silica, silica-alumina, silica-titania, alumina, titania, cation exchange resins such as Amberlyst-15 (trade name for a product of Roam and Haas Co.), etc. Of these, sulfuric acid and cation exchange resins are preferred.

In the Reaction Scheme-1 above, the amount of the aliphatic ketone to be used in the condensation reaction is usually 0.5 to 20 moles, preferably 0.7 to 10 moles per mole of resorcin.

The condensation reaction can proceed in the absence of a solvent or in the presence of an inert solvent. Examples of suitable inert solvent include aromatic hydrocarbons such as benzene, toluene, xylene, etc., aliphatic hydrocarbons such as hexane, heptane, cyclohexane, kerosene, etc., halogenated hydrocarbons such as chloroform, carbon tetrachloride, dichloroethane, etc., nitrobenzene, and the like.

The amount of the inert solvent is usually 1 to 20 parts by weight, preferably 2 to 10 parts by weight per part by weight of resorcin.

The reaction can proceed advantageously with usually 0.005 to 0.2 mole, preferably 0.01 to 0.1 mole of the acidic catalyst per mol of resorcin when Brønsted acids are used as acidic catalyst, and with 1 to 20 parts by weight of the acidic catalyst per 100 parts by weight of resorcin when solid acids are used as acidic catalyst.

The reaction can proceed advantageously at a temperature of 0° to 150° C., preferably 15° to 120° C. for 0.5 to 30 hours, preferably 2 to 20 hours although the reaction time depends on the reaction temperature and other reaction conditions.

The condensation reaction can be conducted by stirring a mixture of resorcin, an aliphatic ketone and an acidic catalyst and optionally an inert solvent to bring the components into contact with each other, and as a result novel compounds of the formula (III) and of the formula (V) are formed.

The compounds of the formula (III) and those of the formula (V) can be separated by subjecting the reaction mixture to conventional procedures including extraction distillation, recrystallization, etc. after removing the starting material and the solvent, if used, by distillation. By the condensation reaction generally 0.5 to 20 moles of the compounds of the formula (V) per mole of the compounds of the formula (III) can be obtained.

Alternatively, the compounds of the formula (III) according to the present invention can be prepared also by the Reaction Scheme-2 below.

Reaction Scheme-2

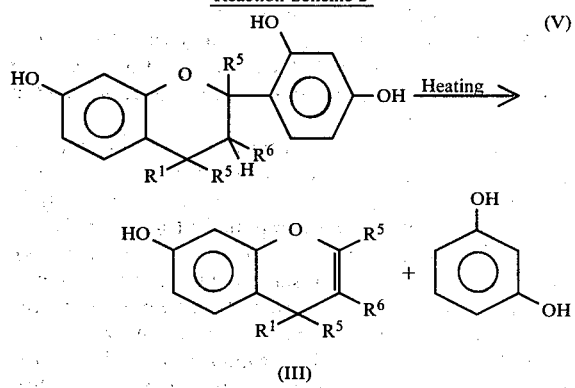

Examples of suitable polyalkyl-2-(2,4-dihydroxyphenyl)-7-hydroxychroman derivative of the formula (V) which can be used as starting material for preparing the compound of the formula (III) by thermal decomposition according to Reaction Scheme-2 include 2,4,4-trimethyl-2-(2,4-dihydroxyphenyl)-7-hydroxychroman, 2,4,4-triethyl-3-methyl-2-(2,4-dihydroxyphenyl)-7-hydroxychroman, 2,4,4-tri-n-propyl-3-ethyl-2-(2,4-dihydroxyphenyl)-7-hydroxychroman, etc. Of these compounds 2,4,4-trimethyl-2-(2,4-dihydroxyphenyl)-7-hydroxychroman is preferred. A mixture of the compounds of the formula (V) can also be used.

Further, the reaction mixture after completion of the condensation reaction according to Reaction Scheme-1 with or without purification can be used as a starting material for preparing compounds of the formula (III) according to Reaction Scheme-2.

Thermal decomposition can be carried out in various manners and can be selected appropriately. For example, it can be performed using a closed thermal decomposition reaction with separating the compounds of the formula (III) and resorcin by distillation, extraction, etc. It is preferred that the compounds of the formula (III) and resorcin be removed out of the reaction system by distillation as soon as they are formed in order to avoid consumption thereof by side reaction. For this purpose, the reaction can be carried out by supplying the starting material for thermal decomposition continuously or in a batch operation to effect thermal decomposition and recovering the resulting compound of the formula (III) resorcin by distillation at a pressure of 1 to 70 mm Hg or, alternatively, recovering them by blowing superheated steam or inert gas into the bottom portion of the distillator to accompany therewith the compounds of the formula (III) resorcin and recover from the head of the distillator.

The thermal decomposition can proceed advantageously at a temperature of 170° to 400° C., preferably 200° to 320° C. Although reaction time for the thermal decomposition may vary depending upon the reaction temperature and the manner in which the thermal decomposition is carried out, generally it ranges from 0.1 to 5 hours.

The thermal decomposition according to Reaction Scheme-2 above can proceed without any catalyst at a satisfactory reaction speed. However, the compound of the formula (III) can be obtained in an increased yield with the use of a catalyst.

As the catalyst, those acidic catalysts which can be employed in the condensation reaction according to Reaction Scheme-2 above in addition to tin and zinc and their compounds can be employed.

The catalyst can be used in an amount of 0.01 to 1 part by weight, preferably 0.05 to 0.5 part by weight of the catalyst per 100 parts by weight of the compound of the formula (V).

After the completion of thermal decomposition, the decomposate can be subjected to conventional purifying procedures, e.g., distillation, extraction, recrystallization, etc. to obtain the compound of formula (III).

Resorcin which is released by the thermal decomposition according to the present invention can be used as starting material for preparing the compounds of the formula (I) according to the present invention.

Of the compounds of the formula (I) according to the present invention, compounds represented by the formula (VI) or (VII) below.

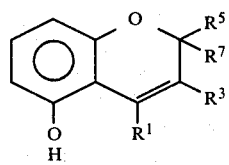
(VI)

wherein $R^1$, $R^3$ and $R^5$ have the same meaning as defined above, and $R^7$ represents an alkyl group having 1 to 3 carbon atoms, or

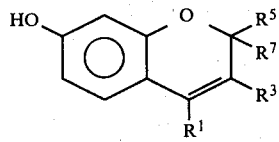
(VII)

wherein $R^1$, $R^3$, $R^5$, and $R^7$ have the same meaning as defined above, with the proviso that $R^1$, $R^5$ and $R^7$ should not be a methyl group simultaneously when $R^3$ represents a hydrogen atom, can be prepared according to Reaction Scheme-3 below.

Reaction Scheme-3

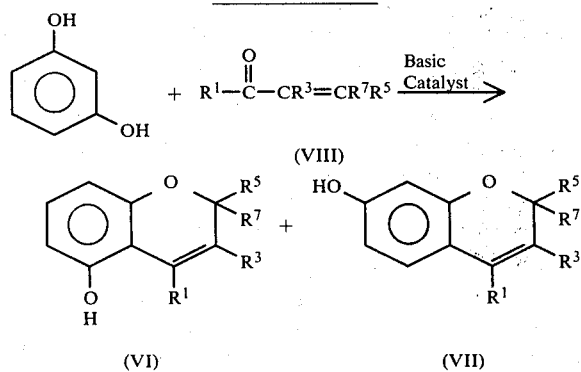

In Reaction Scheme-3 above, $R^1$, $R^3$, $R^5$ and $R^7$ have the same meanings as defined above.

As in Reaction Scheme-1 above, any resorcin can be used as a starting material for preparing the compounds of the formula (VI) or (VII) by condensation reaction according to Reaction Scheme-3 above.

Examples of suitable unsaturated aliphatic ketone which can be used include mesityl oxide, 5-methyl-4-hepten-3-one, 6-methyl-5-nonen-4-one, 5-ethyl-4-methyl-4-hepten-3-one, 2,5,6-trimethyl-4-heptene-3-one, 5-ethyl-2,4,6-trimethyl-4-hepten-3-one, 5-ethyl-4-hepten-3-one, 6-n-propyl-5-nonen-4-one, etc.

Further, since the reaction according to Reaction Scheme-3 is conducted under dehydrating conditions, tertiary alcohols of the formula (IX)

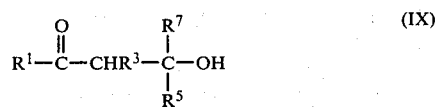
(IX)

wherein $R^1$, $R^3$, $R^5$ and $R^7$ have the same meanings as defined above which can form α,β-unsaturated aliphatic ketones upon dehydration can also be used instead of the α,β-unsaturated aliphatic ketones of the formula (VIII).

Examples of suitable tertiary alcohols of the formula (IX) which can be used in the present invention include 4-hydroxy-4-methyl-pentan-2-one, 5-hydroxy-5-methylheptan-3-one, 6-hydroxy-6-methylnonan-4-one, 5-ethyl-5-hydroxy-4-methylheptan-3-one, 5-hydroxy-2,5,6-trimethylheptan-3-one, 5-ethyl-5-hydroxy-2,4,6-trimethylheptan-3-one, etc.

The reaction can proceed advantageously using α,β-unsaturated aliphatic ketone of the formula (VIII) or tertiary alcohol of the formula (IX) in an amount of 0.5 to 10 mols, preferably 0.8 to 3 mols per mol of resorcin.

Examples of suitable basic catalyst which can be used include basic alkali metal compounds such as lithium hydroxide, sodium hydroxide, potassium hydroxide, lithium oxide, sodium oxide, potassium oxide, lithium carbonate, sodium carbonate, potassium carbonate, lithium hydrogen carbonate, sodium hydrogen carbonate, potassium hydrogen carbonate, lithium methoxide, lithium ethoxide, lithium propoxide, lithium butoxide, sodium methoxide, sodium ethoxide, sodium propoxide, sodium butoxide, potassium methoxide, potassium ethoxide, potassium propoxide, potassium butoxide, methyllithium, ethyllithium, propyllithium, butyllithium, lithium acetate, potassium acetate, etc., basic alkaline earth metal compounds such as magnesium hydroxide, calcium hydroxide, strontium hydroxide, barium hydroxide, magnesium oxide, calcium oxide, strontium oxide, barium oxide, etc., amines such as trimethylamine, triethylamine, tripropylamine, triisopropylamine, tributylamine, pyrrolidine, piperidine, piperazine, pyridine, picoline, lutidine, quinoline, triethylenediamine, 1,8-diazabicyclo[5.4.0]undecene-7, etc., and quaternary ammonium hydroxides such as tetrabutylammonium hydroxide, benzyltrimethylammonium hydroxide, etc. Of these compounds, the basic alkali metal compounds and basic alkaline earth metal compounds are preferred. Most preferred catalyst is alkaline earth metal compound.

Usually, the basic catalyst is used in an amount of 0.001 to 0.3 mol, preferably 0.01 to 0.1 mol per mol of resorcin.

The condensation reaction according to Reaction Scheme-3 can proceed in the absence of a solvent or in the presence of an inert solvent.

Examples of suitable solvent which can be used include aromatic hydrocarbons such as benzene, toluene, xylene, etc., aliphatic hydrocarbons such as hexane, heptane, cyclohexane, kerosene, etc., halogenated hydrocarbons such as chloroform, carbon tetrachloride, dichloroethane, etc., ethers such as anisole, diethylene glycol dimethyl ether, etc., nitrobenzene, and so forth.

Suitably, the proportion of the inert solvent to resorcin is 1 to 10 parts by weight of the solvent per par by weight of resorcin.

The condensation reaction can proceed advantageously at a temperature of 50° to 250° C., preferably 100° to 180° C.

Although reaction time for condensation reaction according to Reaction Scheme-3 may vary depending upon the reaction temperature and other conditions used, generally it can be carried out for 0.5 to 20 hours, preferably 1 to 15 hours.

The condensation reaction can be conducted by stirring a mixture of resorcin, an unsaturated aliphatic ketone of the formula (VIII) or tertiary alcohol of the formula (IX) and an inert solvent, if desired, to bring the components into contact with each other.

The reaction can be carried out in a closed system or in a system where the starting materials are supplied continuously or in a batch operation and the water formed during the reaction is removed out of the reaction system by distillation as an azeotropic mixture with the ketone of the formula (VIII) tertiary alcohol of the formula (IX).

The 5-hydroxy-2H-chromene derivatives of the formula (VI) and 7-hydroxy-2H-chromene derivatives of the formula (VII) obtained can be separated from each other by recovering by distillation the starting materials and solvents, if used, from the reaction mixture after completion of the reaction and subjectioning it to conventional purifying procedures, e.g., extraction, distillation, recrystallization, etc.

By the condensation reaction above, generally 0.3 to 10 mols of the compound of the formula (VII) per mol of the compound of the formula (VI) can be obtained.

When it is desired to obtain the compounds of the formula (VII) as a major product, it is preferred to use the basic alkali metal compounds described above as a catalyst.

The present invention will be further illustrated with reference to examples and experiments, but they are not to be construed as limiting the scope of the present invention.

EXAMPLE 1

In a 100 ml round bottom flask equipped with a condenser was placed 22 g (0.2 mol) of resorcin and 58 g (1.0 mol) of acetone and 0.3 g of concentrated sulfuric acid was added thereto. The resulting mixture was refluxed for 9 hours. After cooling, 10 ml of water was added to the reaction mixture and acetone was distilled off under reduced pressure. To the residue were added 150 ml of aqueous 10% sodium sulfate, 100 ml of methyl isobutyl ketone to separate oily product from aqueous fraction. After washing the oil fraction with water methyl isobutyl ketone was distilled off under reduced pressure to obtain reddish orange viscous liquid. This liquid was mixed with 50 ml of ligroin and heated to separate ligroin-fraction from ligroin-insoluble fraction.

The ligroin-soluble fraction was cooled to precipitate crystals. Recrystallization of the crystals thus obtained from benzene afforded 0.6 g of colorless prismic crystals having a melting point of 118.5°-120° C. The crystal was confirmed to be 2,4,4-trimethyl-7-hydroxy-4H-chromene from the results of $^1H$ nuclear magnetic resonance spectral analysis (100 MHz) described above and those of the following analysis.

(a) Elemental Analysis for $C_{12}H_{14}O_2$

|  | C | H | O |
|---|---|---|---|
| Calculated: | 75.76% | 7.42% | 16.82% |
| Found: | 75.77% | 7.44% | 16.86% |

(b) Mass Spectral Analysis
m/e—190, 175, 160

(c) Infrared Absorption Spectral Analysis (KBr disk)
3600–3,000 $cm^{-1}$—(—OH, broad)
1700 and 1708 $cm^{-1}$—(C=C)

The ligroin-insoluble fraction was mixed with 10 ml of benzene and agitated vigorously under reflux of benzene to precipitate solids, which were collected by filtration and washed with hot benzene to obtain 8.9 g of colorless amorphous powder having a melting point of 235°-237° C. This compound was confirmed to be 2,4,4-trimethyl-2-(2,4-dihydroxyphenyl)-7-hydroxychroman from the results of the following analyses.

(a) Elemental Analysis for $C_{18}H_{20}O_4$

|  | C | H | O |
|---|---|---|---|
| Calculated: | 71.98% | 6.71% | 21.31% |
| Found: | 72.05% | 6.66% | 21.20% |

(b) Mass Spectrum Analysis:
m/e—300, 285, 257, 175, 163, 151, 135

(c) Infrared Absorption Spectral Analysis (KBr disk)
3,510 $cm^{-1}$—(non-associated —OH, sharp)
3,600–3,000 $cm^{-1}$ (associated —OH, broad)

(d) $^1H$ Nuclear Magnetic Resonance Spectral Analysis:
(100 MHz, in $(CD_3)_2CO$, TMS standard)

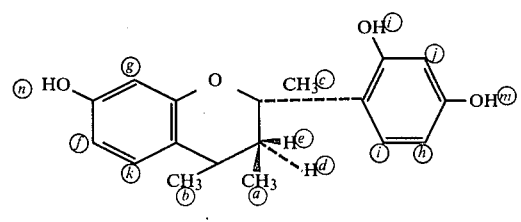

| δ | Attribution |
|---|---|
| 0.80 (S, 3H) | ⓐ |
| 1.20 (S, 3H) | ⓑ |
| 1.65 (S, 3H) | ⓒ |
| 1.85 (d, Jd, e = 13 Hz, 1H) | ⓓ |
| 2.95 (d, Je, d = 13 Hz, 1H) Jf, k = 7 Hz | ⓔ |
| 6.15 (d-d, 1H) Jf, g = 3 Hz, | ⓕ |
| 6.30 (d, Jg, f = 3 Hz, 1H) | ⓖ |
| 6.35 (d, Jh, j = 7 Hz, 1H) | ⓗ |
| 6.40 (S, 1H) | ⓘ |
| 6.95 (d, Jj, h = 7 Hz, 1H) | ⓙ |
| 7.00 (d, Jk, f = 7 Hz, 1H) | ⓚ |
| 8.15 (S, 1H) | ⓛ |
| 8.18 (S, 1H) | ⓜ |

| δ | Attribution |
|---|---|
| 8.45 (S, 1H) | n |

EXAMPLE 2

2,4,4,-Trimethyl-2-(2,4-dihydroxyphenyl)-7-hydroxychroman obtained in Example 1 (6.0 g (20 m mol)) was placed in a 50% ml round bottom flask equipped with a distillator and thermally decomposed under conditions of 200°–310° C. and 10 mmHg. The distillate which was collected was mixed with 50 ml of an aqueous 1% bicarbonate solution and 100 ml of toluene. After dissolution, oil fraction was separated from aqueous fraction. The toluene fraction was washed 3 times with 50 ml of water and dried over anhydrous sodium sulfate followed by removal of toluene by distillation. Recrystallization of the residue from 10 ml of ligroin afforded 3.0 g (yield: 79%) of 2,4,4-trimethyl-7-hydroxy-4H-chromene.

On the other hand, gas chromatographic analysis of the above aqueous bicarbonate fraction and washings revealed resorcin was formed in a yield of 82% (1.8 g).

EXAMPLE 3

A 5 l reactor equipped with an agitating blade, a condenser and a thermometer was charged with nitrogen gas and 2.31 kg (21 mols) of resorcin and 1.22 kg (21 mols) of acetone were placed therein. The mixture was then stirred to dissolved resorcin. The solution was mixed with 180 g of Amberlyst-15 and stirred at room temperature for 30 minutes and then heated to 93° C. in 1 hour. Thereafter, the reaction mixture was stirred at 85° to 93° C. for 2.5 hours to obtain a reddish milk-white viscous liquid (conversion rate of resorcin was 70%).

Then, in a 2 l flask equipped with a 5-tray Oldershaw type distillator was fed intermittently the above-described reaction mixture which was separated from the catalyst by filtration and thermal decomposition was conducted at 200° to 290° C. under reduced pressure of 6 mmHg for 6 hours. The distillate from the top of the distillator was introduced into a mixture of 1 l of an aqueous 3% bicarbonate solution and 0.5 l of toluene and the toluene fraction and aqueous fraction were separated from each other. The aqueous fraction was extracted with 0.5 l of toluene and the extract was added to the toluene fraction. The thus obtained toluene fraction was washed with water to remove residual resorcin and extracted with 3 l of an aqueous 6% sodium hydroxide solution. After washing it with 0.5 l of toluene the alkaline aquous solution thus obtained was neutralized with 50% sulfuric acid and extracted with 1 l of toluene. The toluene fraction thus obtained was washed with water, dried over sodium sulfate, concentrated and distilled under reduced pressure to obtain a fraction having a boiling point of 132° to 134° C./3.5 mmHg. Recrystallization of this fraction from ligroin afforded 530 g (yield: 27%) of 2,4,4-trimethyl-7-hydroxy-4H-chromene.

EXAMPLE 4

The same procedure as Example 3 except that 0.2 g of sulfuric acid per 100 g of the feed material was used as a catalyst for thermal decomposition was repeated to obtain 2,4,4-trimethyl-7-hydroxy-4H-chromene in a yield of 35%.

EXAMPLE 5

In a 300 l flask equipped with an agitating blade, a Dean-Stark condenser and a thermometer were placed 110 g (1 mol) of resorcin, 118 g (1.2 mols) of mesityl oxide and 6.3 g (0.02 mol) of Ba(OH)$_2$.8H$_2$O. The air in the flask was replaced with argon and the reaction mixture was heated at a temperature of 150° to 170° C. under a pressure of 165 to 180 mmHg with stirring while collecting water which was azeotroped with mesityl oxide in the condenser and refluxing mesityl oxide to the flask. After 5 hours conversion rate of resorcin which was determined using gas chromatography was 80%. After cooling, 20 g of 10% sulfuric acid was added to the reaction mixture and the precipitates formed were removed by filtration. To the filtrate was added 100 ml of toluene, washed with water to remove unreacted resorcin, dried over Na$_2$SO$_4$ and concentrated. Then, the concentrate was distilled using a 20-tray Oldershaw type distillator to collect a fraction having a boiling point of 139° to 140° C./7.0 mmHg. Recrystallization of this fraction from hexane-tolene afforded 70 g of colorless granular crystals having a melting point of 113° to 114° C. Formation of 2,2,4-trimethyl-5-hydroxy-2H-chromene in a yield of 37% was confirmed by the above-described $^1$H nuclear magnetic resonance analysis and the following analyses.

(a) Elemental Analysis for C$_{12}$H$_{14}$O$_2$

|  | C | H | O |
|---|---|---|---|
| Calculated: | 75.76% | 7.42% | 16.82% |
| Found: | 75.70% | 7.37% | 16.84% |

(b) Mass Spectral Analysis:
m/e—190, 175, 87.5

(c) Infrared Absorption Spectral Analysis (KBr disk)
3350 cm$^{-1}$ (O—H),—1648 cm$^{-1}$ (C=C)
1609 cm$^{-1}$ (benzene ring)

On the other hand, the fraction having a boiling point of 139°–140° C./2.3 mmHg was collected during distillation and recrystallized from toluene to obtain 38 g of colorless scaly crystals having a melting point of 132° to 133° C. Formation of 2,2,4-trimethyl-7-hydroxy-2H-chromene in a yield of 20% was confirmed by the following analyses.

(a) Elemental Analysis for C$_{12}$H$_{14}$O$_2$

|  | C | H | O |
|---|---|---|---|
| Calculated: | 75.76% | 7.42% | 16.82% |
| Found: | 75.68% | 7.41% | 16.83% |

(b) Mass Spectral Analysis:
m/e—190, 175

(c) Infrared Absorption Spectral Analysis (KBr disk)
3350 cm$^{-1}$ (O—H),—1645 cm$^{-1}$ (C=C)
1615 cm$^{-1}$ (benzene ring)

(d) $^1$H Nuclear Magnetic Resonance Spectral Analysis
(CDCl$_3$, TMS standard)

TABLE 2

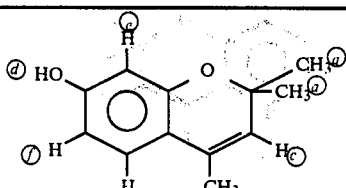

| δ | Attribution |
|---|---|
| 1.38 (S, 6H) | ⓐ |
| 1.95 (S, 3H) | ⓑ |
| 5.27 (S, 1H) | ⓒ |
| 5.55 (S, 1H) | ⓓ |
| 6.32 (d, 1H, J = 2Hz) | ⓔ |
| 6.35 (d-d, 1H, J = 10Hz, 2Hz) | ⓕ |
| 6.98 (d, 1H, J = 10Hz) | ⓖ |

EXAMPLES 6-11

The reaction was repeated in the same manner as in Example 5 except that Ba(OH)$_2$.8H$_2$O was replaced by compounds shown in Table 3 below. The results obtained are also shown in Table 3 below.

TABLE 3

| Example No. | Catalyst Kind | Catalyst Amount (mol) | Reaction Time (hr) | Convention Rate of Resorcin (%) | Yield (A)* | Yield (B)** |
|---|---|---|---|---|---|---|
| 6 | Ca(OH)$_2$ | 0.04 | 6 | 71 | 35 | 16 |
| 7 | Mg(OH)$_2$ | 0.04 | 12 | 50 | 27 | 11 |
| 8 | KOH | 0.03 | 8 | 72 | 6 | 59 |
| 9 | NaOH | 0.04 | 9 | 70 | 7 | 55 |
| 10 | LiOH | 0.04 | 10 | 66 | 6 | 48 |
| 11 | DBU*** | 0.03 | 10 | 51 | 7 | 36 |

*(A) 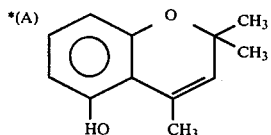

**(B) 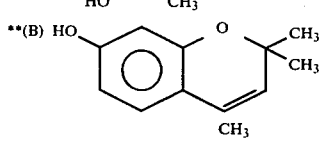

EXAMPLE 12

The reaction was repeated in the same manner as in Example 5 except that 139 g (1.2 mols) of 4-hydroxy-4-methylpentan-2-one was used instead of mesityl oxide. As a result, 2,2,4-trimethyl-5-hydroxy-2H-chromene and 2,2,4-trimethyl-7-hydroxy-2H-chromene were obtained in a yield of 29% and of 11%, respectively. The conversion rate of resorcin was 52%.

EXAMPLE 13

In a 100 ml flask equipped with an agitating blade, a condenser having a water-remover and a thermometer were charged 33 g (0.3 mol) of resorcin, 34 g (0.39 mol) of diethyl ketone and 4 g of Amberlyst 15 as a catalyst. The mixture was reacted at internal temperature of 95° to 100° C. under reduced pressure for 16 hours with stirring while removing water in the form of azeotropic mixture with diethyl ketone. The conversion rate of resorcin was 68%. After cooling, diethyl ether was added to the reaction mixture and the catalyst was removed by filtration. The filtrate was washed with water, dried over sodium sulfate and concentrated. The concentrate was distilled under reduced pressure to collect a fraction having a boiling point of 150° to 158° C./3.4 mmHg. Recrystallization from toluene/hexane (1:1) afforded 25.0 g (yield: 34%) of colorless needle crystals having a melting point of 130° to 133° C. (sublimes). This compound was confirmed to be 2-ethyl-3-methyl-4,4-diethyl-7-hydroxy-4H-chromene by the following analyses.

(a) Elemental Analysis for C$_{16}$H$_{22}$O$_2$

| | C | H | O |
|---|---|---|---|
| Calculated: | 78.01% | 9.00% | 12.99% |
| Found: | 77.90% | 9.03% | 13.00% |

(b) Mass Spectral Analysis:
m/e—246, 217, 201

(c) Infrared Absorption Spectral Analysis (KBr disk):
3300 cm$^{-1}$ (—OH, broad), —1682 cm$^{-1}$ (C=C)

Experiment 1

Herbicidal Effect on Paddy Field Weed

A paddy field soil was filled in a 1/5,000 a pot. After plowing the soil and making its surface, even, 10 seeds of *Cyperus difformis* were sown and water was filled in the pot at a depth of 3 cm. Next day, wettable powder consisting of a mixture of 50% by weight of 2,4,4-trimethyl-7-hydroxy-4H-chromene, 45% by weight of diatomaceous earth, 2% by weight of sodium dinaphthylmethanedisulfonate and sodium ligninsulfonate was applied uniformly onto the water surface in an amount of 5 kg/ha as active ingredient. After allowing the pot to stand in a green house for 20 days the germination ratio of *Cyperus difformis* was recorded which was 20%. On the other hand, the germination ratio was 100% when 2,2,4-trimethyl-7-hydroxy-2H-chromene, known compound, was applied in the same manner as above instead of 2,4,4-trimethyl-7-hydroxy-4H-chromene of the present invention.

EXPERIMENT 2

Herbicidal Effect on Upland Field Weed

Onto lambsquarters of two leaves period was uniformly applied an emulsion containing 0.4% by weight of 2,4,4-trimethyl-7-hydroxy-4H-chromene in an amount of 1,000 l/ha. After 15 days it was observed that 90% of lambsquarters were withered. On the other hand, no death (withering) of lambsquarters was observed when 2,2,4-trimethyl-7-hydroxy-2H-chromene, known compound, instead of 2,4,4-trimethyl-7-hydroxy-4H-chromene of the present invention was applied in the same manner as above.

While the invention has been described in detail and with reference to specific embodiments thereof, it will be apparent to one skilled in the art that various changes and modifications can be made therein without departing from the spirit and scope thereof.

What is claimed is:

1. A compound represented by the formula (III)

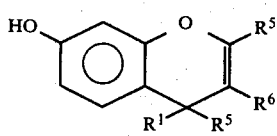 (III)

wherein $R^1$ and $R^5$ each represents an alkyl group having 1 to 3 carbon atoms, and $R^6$ represents a hydrogen atom or an alkyl group having a carbon atom number smaller than that of $R^1$ by one.

2. A compound represented by the formula (VI)

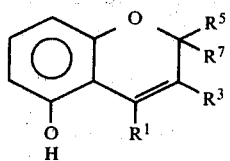 (VI)

wherein $R^1$ and $R^5$ and $R^7$ each represents an alkyl group having 1 to 3 carbon atoms, and $R^3$ represents a hydrogen atom or an alkyl group having 1 to 3 carbon atoms.

3. 2,2,4-Trimethyl-5-hydroxy-2H-chromene as claimed in claim 1.

4. 2,4,4-Trimethyl-7-hydroxy-4H-chromene as claimed in claim 2.

* * * * *